(12) United States Patent
De Angelis et al.

(10) Patent No.: US 6,936,737 B2
(45) Date of Patent: Aug. 30, 2005

(54) PROCESS FOR THE SYNTHESIS OF MIXTURES OF METHANE DIPHENYL DIAMINE AND ITS HIGHER HOMOLOGUES WITH A CONTROLLED ISOMER DISTRIBUTION

(75) Inventors: Alberto De Angelis, Legnano (IT); Cristina Flego, Milan (IT); Otello Farias, Rome (IT); Aldo Bosetti, Vercelli (IT)

(73) Assignee: Dow Global Technologies Inc., Midland, MI (US)

( * ) Notice: Subject to any disclaimer, the term of this patent is extended or adjusted under 35 U.S.C. 154(b) by 82 days.

(21) Appl. No.: 10/363,881

(22) PCT Filed: Sep. 7, 2001

(86) PCT No.: PCT/EP01/10369
§ 371 (c)(1),
(2), (4) Date: Sep. 5, 2003

(87) PCT Pub. No.: WO02/20458
PCT Pub. Date: Mar. 14, 2002

(65) Prior Publication Data
US 2004/0029971 A1 Feb. 12, 2004

(30) Foreign Application Priority Data
Sep. 7, 2000  (IT) .................................. MI2000A1959

(51) Int. Cl.$^7$ .............................................. C07C 209/54
(52) U.S. Cl. ...................................... 564/330; 564/332
(58) Field of Search .................................. 564/330, 332

(56) References Cited

U.S. PATENT DOCUMENTS

| | | | | |
|---|---|---|---|---|
| 3,442,795 A | * | 5/1969 | Rosinski et al. | ........ 208/120.05 |
| 3,728,408 A | * | 4/1973 | Tobias | ......................... 568/822 |
| 4,039,580 A | * | 8/1977 | Frulla et al. | ................. 564/332 |
| 4,039,581 A | * | 8/1977 | Frulla et al. | ................. 564/332 |
| 4,294,987 A | * | 10/1981 | Prather et al. | ............... 564/331 |
| 5,241,119 A | * | 8/1993 | Clerici et al. | ................ 564/332 |

FOREIGN PATENT DOCUMENTS

| | | | | |
|---|---|---|---|---|
| EP | 0264744 | * | 4/1988 | ........... C07C/85/24 |
| EP | 0329367 A2 | * | 8/1989 | ........... C07C/85/24 |
| EP | 1055663 A1 | * | 11/2000 | ......... C07C/209/78 |

* cited by examiner

*Primary Examiner*—Brian Davis

(57) ABSTRACT

A process for preparing methane diphenyl diamine (MDA) or a mixture of methane diphenyl diamine (MDA) and its higher homologues with a controlled isomer distribution using a silanised zeolite have "shape selectivity". The mixture contains compounds having the following general formula (I): where R represents a hydrogen atom or a $C_1$ to $C_8$ (iso) alkyl group, a $C_4$ to $C_{10}$ cycloalkyl group or a $C_6$ to $C_{12}$ aromatic group and n is a whole number greater than or equal to one so as to give a functionally of 2 to 6.

17 Claims, No Drawings

PROCESS FOR THE SYNTHESIS OF MIXTURES OF METHANE DIPHENYL DIAMINE AND ITS HIGHER HOMOLOGUES WITH A CONTROLLED ISOMER DISTRIBUTION

This invention relates to a process for preparing methane diphenyl diamine (MDA) or a mixture of methane diphenyl diamine (MDA) and its higher homologues with a controlled isomer distribution. More specifically, this invention relates to a process for the preparation of MDA or of mixtures of MDA and its higher homologues, in which the said mixture contains compounds having the following general formula (I):

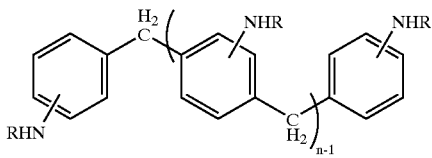

where R represents a hydrogen atom or a $C_1$ to $C_8$ (iso)alkyl group, a $C_4$ to $C_{10}$ cycloalkyl group or a $C_6$ to $C_{12}$ aromatic group and n is a whole number greater than or equal to one so as to give a functionality of 2 to 6, in which it is possible to control the concentration of dimeric products, in particular of isomer 4.4'-MDA with respect to isomers 2.4'-MDA and 2.2'-MDA.

Methane diphenyl diamine or the methane diphenyl diamine mixtures are used as intermediates in the preparation of the corresponding methane diphenyl diisocyanate (MDI), in turn used in the synthesis of a series of polymers for example polyurethanes, thermoplastic polymers and epoxy resins.

Methane diphenyl diamine is normally produced from aniline or from one of its derivatives by condensation with formaldehyde in the presence of solutions of strong acids, such as hydrochloric acid, sulphuric acid and phosphoric acid, as described, for example, in U.S. Pat. Nos. 2,683,730, 3,277,173, 3,344,162; 3,362,979 or in H. Ulrich, "Chemistry and Technology of Isocyanates" John Wiley and Sons, USA, 1996. The operating conditions, necessary to obtain a product with the specific structural characteristics and without the formation of undesirable amounts of by-products, demand the use of a considerable quantity of strong acid and consequently the use of materials in the equipment which are capable of resisting such acids. Further, after the MDA has been synthesised, a corresponding amount of base material (typically soda) is needed to neutralise the acid used, leading to the formation of consistent quantities of salts contaminated by aromatic products to be discharged. All these requirements result in an increase in production costs.

Production processes based on using strong acid catalysts in which, for example the synthesis is carried out in the presence of hydrophobic solvents in order to totally or partially recycle the acid catalyst in an aqueous stage are known. These types of procedures are described, for example, in U.S. Pat. No. 4,924,028 and U.S. Pat. No. 4,914,236.

To improve the process the use of other solvents (generally chlorinated) different from the initial substrate has been contemplated. However chlorinated solvents may increase the risk of environmental damage.

U.S. Pat. No. 4,039,580 and U.S. Pat. No. 4,039,581 describe the use of reusable solid acids, in particular clays, in the synthesis of MDA from aniline and formaldehyde. In particular, the process in U.S. Pat. No. 4,039,581 allows for the low temperature pre-condensation between aniline and formaldehyde and the elimination of water and methanol. Aminals are also obtained which come into contact with the solid acid catalyst, at a temperature of between 20 and 55° C. to produce the corresponding benzylamines. The benzylamines is then converted to the end products.

U.S. Pat. No. 4,071,558 describes an analogous approach using Superfiltrol type of solid acid catalysts, in which the distribution of the dimeric products is modulated, in particular of isomer 2.4'-MDA, based on selecting the operating conditions of condensation.

The processes in U.S. Pat. No. 4,039,580 and U.S. Pat. No. 4,071,558 illustrate the disadvantage with acid catalysts as the water content is suitably not greater than 3% in weight, and preferably less than 0.15% in weight, in order to avoid deactivation of the catalyst. Clays also present problems because they may be reused for a limited number of times and, since their origin is natural and not synthetic, consistent performance cannot be entirely reproduced in accordance with the sample batches.

The Applicants have found a procedure for the preparation of MDA in a mixture with its higher homologues which allows distribution between the main dimeric products to vary over a wide range and reduce or avoid disadvantages with known processes. The ability to control the variation in the distribution allows a range of derivative products to be obtained such as isocyanates, obtained by the phosgenation of MDA, with characteristic features, and which may be tailored as appropriate.

The process, which is the object of the present invention, is based on the silanation of a zeolite catalyst in acid state, described below, with alkyl silanic compounds, which may be linear, branched or cyclic. It is believed that the silanating agent reacts with the acid sites and the defective sites on the external surface of the zeolite silica by being hydrolysed and also being bound to the surface but due to its size, does not enter the pores. As a result of calcination the surface of the zeolite becomes covered, at least in part, with silica, as previously confirmed by R. W. Weber et al. in "The chemical vapour and liquid deposition of tetraethoxysilane on external surface of ZSM-5", Microporous Materials 23 (1998) 179–187.

The silanation process may affect the size of the aperture of the pores and provide a "shape selectivity" effect so influencing the distribution of the reaction products.

Surprisingly it has been found that this "shape selectivity" effect is also present in the catalysed acid synthesis of the different isomers of the MDA, providing improved selectivity to the isomers having less steric hindrance, namely 4.4'-MDA. This distribution variation in the isomers may be modified at broad intervals either by changing the method of operation of the silanation treatment, or by varying the amount of silica bound to the surface of the zeolite, and by repeating the treatment itself whilst maintaining acceptable catalyst life.

The object of the invention provides a process for the preparation of MDA or a mixture of MDA and its higher homologues having the general formula (I):

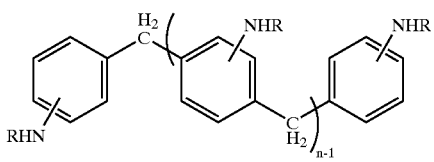

where R is independently selected from hydrogen, a $C_1$ to $C_8$ alkyl group, a $C_4$ to $C_{10}$ cycloalkyl group and a $C_6$ to $C_{12}$ aromatic group and n is a whole number greater than, or equal to one, suitably from 1 to 5 so as to give a functionality from 2 and 6, which comprises carrying out the re-arrangement reaction of the intermediate having general formula (II):

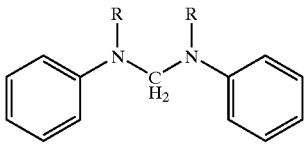

in the presence of a zeolite in acid form with a "spaciousness index" from 2.5 to 19 modified on the surface by one or more organic silicon compounds having the general formula $Si(OX)_4$ or $SiX_4$, in which X represents independently a $C_1$ to $C_{20}$ alkyl group, a $C_4$ to $C_{20}$ cycloalkyl group, or a $C_6$ to $C_{20}$ aromatic or alkyl-aromatic group, optionally substituted with one or more halogen atoms which zeolite has been calcined, preferably at a temperature of at least 400° C. and especially 500° C. or more.

Reference to "alkyl" herein shall be taken to include linear alkyl and branched or "iso" alkyl groups unless otherwise stated.

The "spaciousness index" is a parameter which gives the true measurement of the width of the pores in porous materials, such as zeolites. The "spaciousness index" is a parameter described in literature as, for example, in U.S. Pat. No. 4,795,847 and in "Zeolites and Related Microporous Material: State of the Art 1994", Studies in Surface Science and Catalysis, vol. 84, 37, 1994, Elsevier Science B.V.; "Zeolite: Facts, Figures, Future", 1989, 1115, Elsevier Science Publishers, B.V.

According to the present invention, zeolites with a preferred "spaciousness index" of between 2.5 and 19 suitably are crystalline material having the composition (II):

where x is less than 1, p is a whole number greater than or equal to 1, preferably from 1 to 20, M is a metal from Groups IA or IIA, or is a lanthanide, n is the valency of M, and where M may be partially or totally exchanged for $H^+$, $(NH_4)^+$, or for $(NR'_4)^+$ where R' is an alkyl group, for example $C_1$ to $C_4$ alkyl, or an aryl group.

Examples of zeolite which fall under the general formula (III) and which have a "spaciousness index" from 2.5 to 19 include beta zeolite, mordenite, ZSM-12, MCM-22 and ERB-1. Particular preference is given to beta zeolite, for example as described in U.S. Pat. No. 3,308,069 with a "spaciousness index" of 19.

The silanation treatment of the acid zeolites suitably is carried out by contacting, in particular immersing, at least in part, the solid zeolite, for example in particulate form, in a liquid comprising an organic silicon compound of formula $Si(OX)_4$ and/or $SiX_4$, as defined herein and preferably silicon compound as set out in the examples. The liquid may be neat or diluted in a solvent. Suitably the immersion process is carried out at a temperature of 20 to 80° C. At the end of this immersion stage, the organic silicon compound which has not reacted preferably is removed, at least in part, desirably by distillation under a vacuum. Suitably the remaining solid is calcined, preferably at a temperature of 500 to 600° C. The silanation treatment may be repeated two or more times, for example 3 to 5 times, with each immersion being followed by the corresponding removal of liquid and calcination stage. The organic silicon compound may be the same or different in each treatment.

The zeolite used to prepare the silanated catalyst in the present invention is suitably in acid form, that is, in the form in which hydrogen ions occupy most of the cationic locations. In the silanation treatment the zeolite may be used "as is" or may be modified before the treatment by the partial isomorphic substitution of aluminium by a metal selected from boron, iron and gallium. At the end of the silanation treatment, the catalyst may be used "as is" or in combination with a binder, for example alumina. The catalyst may be shaped in extruded tablets, for example as described in EP-A-847,802, or in any other suitable form.

Suitably, the rearrangement reaction is carried out at a temperature of 50 to 250° C., preferably from 120 to 200° C., in the presence of a solvent. Examples of suitable solvents include optionally substituted aliphatic hydrocarbons, optionally substituted aromatic hydrocarbons, halogenated aromatic hydrocarbons and aniline. Examples of solvents which are particularly suitable are aniline and aromatic chlorinated hydrocarbons such as m-dichlorobenzene and chlorobenzene.

The intermediate in general formula (II) is a product referred to in the literature, in particular when R is hydrogen. This intermediate may be obtained by condensing aniline, or derived from aniline in which R is different from hydrogen, with formaldehyde, or a compound capable of producing formaldehyde under reaction conditions. In particular, formaldehyde may be used in an aqueous solution such as formaldehyde in an oligomerous state (for example trioxane), dissolved in a solvent, suitably with aniline/formaldehyde molar ratios of 2 to 10, preferably from 3 to 5. At the end of the synthesis, the intermediate in formula (II) is desirably separated by known methods, for example physical separation and distillation. The product thus obtained may contain water but the water content suitably is 3% or less by weight and preferably 1.5% or less.

In accordance with a further aspect the invention provides a process for the preparation of methane diphenyl diamine in general formula (I) in which the rearrangement reaction may be carried out by contacting the zeolite catalyst with a reaction mixture comprising aniline, or a derivative of aniline, and formaldehyde, or a compound capable of producing formaldehyde under the reaction conditions. In this case, the aniline, or its derivative, is preferably present in stoichiometric excess and may act as both a reagent and a solvent for the reaction at the same time.

According to the present invention, the rearrangement reaction may be carried out discontinuously, continuously or semi-continuously at ambient pressure or elevated pressure such as to maintain the reactive system in a liquid state.

In a preferred embodiment, a procedure for the production of a compound having general formula (I) comprises:
(a) reacting aniline, or a derivative of aniline and formaldehyde, or a precursor of formaldehyde, so as to form an amine of formula (II) optionally in a solvent, preferably aniline or its derivative in the event that the aniline or its derivative is used in sufficient excess;

(b) removing water if present, from the amine (II) to a residual concentration of water of 3% or less by weight of the amine (II);
(c) optionally diluting the product of step (b) in a solvent;
(d) isomerising the amine (II) by feeding it into a reaction zone, preferably one or more fixed bed reactors, containing a zeolite in acid form with a "spaciousness index" of 2.5 to 19, modified on its surface, preferably by an immersion process, by one or more organic silicon compounds with the general formula $Si(OX)_4$ and/or $SiX_4$, in which X represents independently a $C_1$ to $C_{20}$ alkyl group, a $C_4$ to $C_{20}$ cycloalkyl group, or a $C_6$ to $C_{20}$ aromatic or alkyl-aromatic group, optionally substituted with one or more halogen atoms which zeolite has been calcined, preferably at a temperature of at least 400° C. and especially 500° C. or more, and wherein the reaction zone in step d) is at an ambient pressure or such as to maintain the reagent mixture in a liquid state and, preferably at a temperature of 50 to 250° C., more preferably 120 to 200° C.;
(e) recovering the methane diphenyl diamine, and/or its higher homologues, preferably by a purification process, for example, distillation.

According to the present invention, the reagents in step (a) may be fed discontinuously, continuously or semi-continuously to the reaction zone, suitably beginning with aniline and formaldehyde (or their derivatives or precursors). The pre-condensed material is subsequently fed into the reaction zone, preferably a fixed bed reactor, containing the silanated solid acid catalyst, after water has been removed.

In step a), the reactants suitably are used in proportions from between 2 to 15 moles of aniline or a derivative of it per mole of formaldehyde. Preferably the reaction in step (a) is carried out at a temperature of between 10 to 60° C. and in the absence of an acid catalyst.

The pre-condensed amine (II) may be fed to the reaction zone by staggering by using a vertical reactor fitted with two or more lateral inlets.

Suitably, the separation of water from the amine (II) is carried out in accordance with conventional techniques such as decanting or distillation. The separation may be carried out at variable temperatures or pressures according to the degree of residual water which it is desired to have in the amine solution (II). Separating the water may also be carried out by using a combination of the techniques referred to, such as, for example, decanting followed by distillation.

At the end of the rearrangement reaction of the amine (II), the distribution of the components in the composition of the mixture obtained after isomerisation may subsequently be modified by totally or partially recycling the mixture itself in the amine (II) synthesis reaction zone in step a) and/or in the rearrangement or isomerisation reaction zone.

A further process for the production of a compound having general formula (I) comprises reacting aniline, or one of its derivatives, and formaldehyde, or one of its precursors, in one single reaction step, preferably in a complete mixing reactor, in the presence of a zeolite in acid form with a "spaciousness index" of 2.5 to 19 modified on the surface by one or more organic silicon compounds having the general formula $Si(OX)_4$ or $SiX_4$, in which X represents independently a $C_1$ to $C_{20}$ alkyl group, a $C_4$ to $C_{20}$ cycloalkyl group, or a $C_6$ to $C_{20}$ aromatic or alkyl-aromatic group, optionally substituted with one or more halogen atoms which zeolite has been calcined, preferably at a temperature of at least 400° C. and especially 500° C. or more, and continually removing, preferably continually, for example by distilling, the water of reaction or additional water with one or more reagents.

Suitably, the order of the single stage process is based on the use of slurry reactors, either shaken or bubbled. Both the reagents, aniline (or one of its derivatives), and formaldehyde, (or one of its precursors), and the solid acid catalyst, optionally in the presence of a solvent which preferably comprises excess aniline or its derivative are fed, preferably simultaneously into a slurry reactor. Feeding of the reagents may be carried out continuously or by staggering the addition along with one or more components of the reaction mixture.

The aniline/formaldehyde molar ratio used suitably is from 2 to 15, and preferably from 3 to 5. Suitably the reaction temperature is from 50 to 250° C. and preferably from 120 to 200° C. Suitably, the pressure is that generated by the water with the reagents, or that which is generated during the reaction. Preferably the reaction mixture is continually agitated by an appropriate distillation system fitted to the reactor. The residence times in the liquid stage are suitably from 0.5 to 10 hours and preferably from 1 to 8 hours.

In the event the catalyst is to be replaced, the catalyst suitably is totally replaced within a period of 5 hours to a period of 30 hours. Preferably, the catalyst/load weight ratio is between 1/20 and 1/300.

At the end of reaction, the catalyst suitably is filtered, and any excess aniline (and any residual water and/or solvent which may remain) are removed from the required product by conventional techniques, for example by distillation.

The mixture of methane diphenyl diamine and/or its higher homologues synthesised in accordance with the process described above may be converted into the corresponding mixture of isocyanates in accordance with the techniques referred to.

In order to understand the present invention better and to put it into practice, there follow some examples which are for the purposes of illustration and are not exhaustive.

EXAMPLE 1
Amine Synthesis (Reaction Intermediate)
The reaction intermediate in the formula:

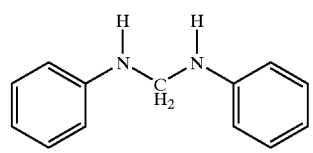

is prepared by condensation between aniline and formaldehyde. In particular, an aqueous solution with 37% formaldehyde is fed, while being stirred, into a reaction vessel containing aniline in order to have a formaldehyde/aniline molar ratio equal to four: the temperature is slowly raised to 50° C.

When the solution has been added, it is continued to be stirred for one hour, and then the organic stage consisting of amine and the aniline which has not reacted are then separated by a separator funnel. The organic stage is then dried to a maximum water content of 1.25% and retained for later use.

EXAMPLE 2
Synthesis of Beta Zeolite Silanised with TEOS
5 g of beta zeolite, CP 806BL'PQ (ammoniacal state) with a molar ratio of $SiO_2/Al_2O_3=25$, and a spaciousness index of 19, previously treated at 550° C. in an air flow in order to obtain the acid state from the ammonium state, and 50 ml of a tetraethyl orthosilicate solution (TEOS) at 5% hexane are fed into a glass flask.

This suspension is shaken for 24 hours at an ambient temperature, and the solvent and the TEOS which has not reacted are then separated in a vacuum.

The material obtained in this way, in the form of a white powder, is calcined at 550° C. in an air flow for 5 hours. A calcine free from carbon residues is then obtained, the molar ratio of $SiO_2/Al_2O_3$ is equal to 55.41.

EXAMPLE 3
Synthesis of Beta Zeolite Silanised with TPOS 5 g of beta zeolite, as described in example 2, previously treated at 550° C. in an air flow in order to obtain the acid state from the ammoniacal state, and 50 ml of a tetrapropyl orthosilicate solution (TPOS) at 5% hexane are fed into a glass flask.

This suspension is shaken for 24 hours at an ambient temperature, and the solvent and the TPOS which has not reacted are then separated in a vacuum.

The material obtained in this way, in the form of a white powder, is calcined at 550° C. in an air flow for 5 hours. A calcine free from carbon residues is then obtained, the molar ratio of $SiO_2/Al_2O_3$ is equal to 50.30.

EXAMPLE 4
Synthesis of Beta Zeolite Silanised with TBOS 5 g of beta zeolite, as described in example 2, previously treated at 550° C. in an air flow in order to obtain the acid state from the ammoniacal state, and 50 ml of a tetrabutyl orthosilicate solution (TBOS) at 5% hexane are fed into a glass flask.

This suspension is shaken for 24 hours at an ambient temperature, and the solvent and the TBOS which has not reacted are then separated in a vacuum.

The material obtained in this way, in the form of a white powder, is calcined at 550° C. in an air flow for 5 hours. A calcine free from carbon residues is then obtained, the molar ratio of $SiO_2/Al_2O_3$ is equal to 29.49.

EXAMPLE 5
Synthesis of Beta Zeolite Silanised with OMTS 5 g of beta zeolite, as described in example 2, previously treated at 550° C. in an air flow in order to obtain the acid state from the ammoniacal state, and 50 ml of an octamethyl cyclotetrasiloxane solution (OMTS) at 5% hexane are fed into a glass flask.

This suspension is shaken for 24 hours at an ambient temperature, and the solvent and the OMTS which has not reacted are then separated in a vacuum.

The material obtained in this way, in the form of a white powder, is calcined at 550° C. in an air flow for 5 hours. A calcine free from carbon residues is then obtained, the molar ratio of $SiO_2/Al_2O_3$ is equal to 28.67.

EXAMPLE 6
Synthesis of Beta Zeolite Silanised Twice with OMTS 5 g of beta zeolite, as described in example 2, previously treated at 550° C. in an air flow in order to obtain the acid state from the ammoniacal state, and 50 ml of an octamethyl cyclotetrasiloxane solution (OMTS) at 5% hexane are fed into a glass flask.

This suspension is shaken for 24 hours at an ambient temperature, and the solvent and the OMTS which has not reacted are then separated in a vacuum.

The material obtained in this way, in the form of a white powder, is calcined at 550° C. in an air flow for 5 hours.

A white powder is obtained which is subjected to the silanisation process for a second time. A calcine free from carbon residues is then obtained, the molar ratio of $SiO_2/Al_2O_3$ is equal to 28.70.

EXAMPLE 7
Synthesis of Beta Zeolite Silanised 3 Times with OMTS 5 g of beta zeolite, as described in example 2, previously treated at 550° C. in an air flow in order to obtain the acid state from the ammoniacal state, and 50 ml of an octamethyl cyclotetrasiloxane solution (OMTS) at 5% hexane are fed into a glass flask.

This suspension is shaken for 24 hours at an ambient temperature, and the solvent and the OMTS which has not reacted are then separated in a vacuum.

The material obtained in this way, in the form of a white powder, is calcined at 550° C. in an air flow for 5 hours.

A white powder is obtained which is subjected to the silanisation process twice more. A calcine free from carbon residues is then obtained, the molar ratio of $SiO_2/Al_2O_3$ is equal to 29.55.

EXAMPLE 8
Synthesis of Beta Zeolite Heat Silanised with OMTS 5 g of beta zeolite, as described in example 2, previously treated at 550° C. in an air flow in order to obtain the acid state from the ammoniacal state, and 50 ml of an octamethyl cyclotetrasiloxane solution (OMTS) at 5% hexane are fed into a glass flask.

This suspension is shaken for 6 hours at 60° C., and the solvent and the OMTS which has not reacted are separated in a vacuum.

The material obtained in this way, in the form of a white powder, is calcined at 550° C. in an air flow for 5 hours. A calcine free from carbon residues is then obtained, the molar ratio of $SiO_2/Al_2O_3$ is equal to 52.61.

EXAMPLE 9
Synthesis of Beta Zeolite Silanised with Pure OMTS 5 g of beta zeolite, as described in example 2, previously treated at 550° C. in an air flow in order to obtain the acid state from the ammoniacal state, and 50 ml of pure octamethyl cyclotetrasiloxane (OMTS) are fed into a glass flask.

This suspension is shaken for 24 hours at an ambient temperature, and the OMTS which has not reacted is separated in a vacuum.

The material obtained in this way, in the form of a white powder, is calcined at 550° C. in an air flow for 5 hours. A calcine free from carbon residues is then obtained, the molar ratio of $SiO_2/Al_2O_3$ is equal to 54.34.

EXAMPLE 10
Synthesis of Zeolite ZSM-12 Silanised with OMTS 5 g of zeolite ZSM-12, prepared in accordance with U.S. Pat. No. 3,832,449 (1974) of the Mobil Oil Corporation, with a molar ratio of $SiO_2/Al_2O_3=102$, a spaciousness index of 3, and 50 ml of an octamethyl cyclotetrasiloxane (OMTS) solution at 5% hexane are fed into a glass flask.

This suspension is shaken for 24 hours at an ambient temperature, and the solvent and the OMTS which has not reacted are separated in a vacuum.

The material obtained in this way, in the form of a white powder, is calcined at 550° C. in an air flow for 5 hours. A calcine free from carbon residues is then obtained, the molar ratio of $SiO_2/Al_2O_3$ is equal to 197.70.

EXAMPLE 11 (COMPARATIVE)
Catalytic Test with Untreated Beta Zeolite 4 g of amine, 10 g of aniline and 125 mg of beta zeolite, CP 806BL (in ammoniacal form), with a molar ratio of $SiO_2/Al_2O_3=25$, previously treated at 550° C. in an air flow in order to obtain zeolite in acid form, are fed into a glass autoclave.

The autoclave is closed and is stirred at 150° C. for 6 hours. The mass is then cooled at ambient temperature and the reaction solvent is removed by distillation at a reduced pressure.

The reaction product is analysed by H.P.L.C. according to the method of analysis described in the Journal für Praktische Chemie, Band 328, Heft 1, 1986, 142–148.
Conversion: 100%;
selectivity at 4.4'-MDA: 54.99%;
selectivity at 2.4'+2.2'-MDA: 24.67%;
molar ratio 4.4'/(2.4'+2.2'): 2.2
trimers: 11.95%;
heavy particles: 10.13%.

EXAMPLE 12
Catalytic Test with Beta Zeolite Treated with TEOS 4 g of amine, 10 g of aniline and 125 mg of beta zeolite in acid form treated with TEOS, as described in example 2, are fed into a glass autoclave. The autoclave is closed and is stirred at 150° C. for 6 hours.

The mass is then cooled at ambient temperature and the reaction solvent is removed by distillation at a reduced pressure.

The reaction product is analysed by H.P.L.C. according to the method of analysis described in the Journal für Praktische Chemie, Band 328,
Heft 1, 1986, 142–148.
Conversion: 100%;
selectivity at 4.4'-MDA: 49.06%;
selectivity at 2.4'+2.2'-MDA: 18.62%;
molar ratio 4.4'/(2.4'+2.2'): 2.63
trimers: 23.5%;
heavy particles: 8.55%.

EXAMPLE 13
Catalytic Test with Beta Zeolite Treated with TPOS.

4 g of amine, 10 g of aniline and 125 mg of beta zeolite in acid form treated with TPOS, as described in example 3, are fed into a glass autoclave. The autoclave is closed and is stirred at 150° C. for 6 hours.

The mass is then cooled at ambient temperature and the reaction solvent is removed by distillation at a reduced pressure.

The reaction product is analysed by H.P.L.C. according to the method of analysis described in the Journal für Praktische Chemie, Band 328,
Heft 1, 1986, 142–148.
Conversion: 100%;
selectivity at 4.4'-MDA: 54.13%;
selectivity at 2.4'+2.2'-MDA: 20.14%;
molar ratio 4.4'/(2.4'+2.2'): 2.69
trimers: 19.72%;
heavy particles: 5.69%.

EXAMPLE 14
Catalytic Test with Beta Zeolite Treated with TBOS 4 g of amine, 10 g of aniline and 125 mg of beta zeolite in acid form treated with TBOS, as described in example 4, are fed into a glass autoclave. The autoclave is closed and is stirred at 150° C. for 6 hours.

The mass is then cooled at ambient temperature and the reaction solvent is removed by distillation at a reduced pressure.

The reaction product is analysed by H.P.L.C. according to the method of analysis described in the Journal für Praktische Chemie, Band 328,
Heft 1, 1986, 142–148.
Conversion: 100%;
selectivity at 4.4'-MDA: 54.81%;
selectivity at 2.4'+2.2'-MDA: 19.99%;
molar ratio 4.4'/(2.4'+2.2'): 2.74
trimers: 15.45%;
heavy particles: 8.55%.

EXAMPLE 15
Catalytic Test with Beta Zeolite Treated with OMTS.

4 g of amine, 10 g of aniline and 125 mg of beta zeolite in acid form treated with OMTS, as described in example 5, are fed into a glass autoclave. The autoclave is closed and is stirred at 150° C. for 6 hours.

The mass is then cooled at ambient temperature and the reaction solvent is removed by distillation at a reduced pressure.

The reaction product is analysed by H.P.L.C. according to the method of analysis described in the Journal für Praktische Chemie, Band 328,
Heft 1, 1986, 142–148.
Conversion: 100%;
selectivity at 4.4'-MDA: 53.45%;
selectivity at 2.4'+2.2'-MDA: 11.90%;
molar ratio 4.4'/(2.4'+2.2'): 4.49
trimers: 15.135%;
heavy particles: 16.63%.

EXAMPLE 16
Catalytic Test with Beta Zeolite Treated Twice with OMTS.

4 g of amine, 10 g of aniline and 125 mg of beta zeolite in acid form treated with OMTS, as described in example 6, are fed into a glass autoclave. The autoclave is closed and is stirred at 150° C. for 6 hours.

The mass is then cooled at ambient temperature and the reaction solvent is removed by distillation at a reduced pressure.

The reaction product is analysed by H.P.L.C. according to the method described in the Journal für Praktische Chemie, Band 328,
Heft 1, 1986, 142–148.
Conversion: 100%;
selectivity at 4.4'-DAD: 57.10%;
selectivity at 2.4'+2.2'-DAD: 10.15%;
molar ratio 4.4'/(2.4'+2.2'): 5.63
trimers: 23.83%;
heavy particles: 8.38%.

EXAMPLE 17
Catalytic Test with Beta Zeolite Treated Three Times with OMTS.

4 g of amine, 10 g of aniline and 125 mg of beta zeolite in acid form treated with OMTS, as described in example 7, are fed into a glass autoclave. The autoclave is closed and is stirred at 150° C. for 6 hours.

The mass is then cooled at ambient temperature and the reaction solvent is removed by distillation at a reduced pressure.

The reaction product is analysed by H.P.L.C. according to the method of analysis described in the Journal für Praktische Chemie, Band 328,
Heft 1, 1986, 142–148.
Conversion: 100%;
selectivity at 4.4'-MDA: 58.10%;
selectivity at 2.4'+2.2'-MDA: 10.07%;
molar ratio 4.4'/(2.4'+2.2'): 5.77
trimers: 21.67%;
heavy particles: 9.35%.

EXAMPLE 18
Catalytic Test with Beta Zeolite Heat Treated with OMTS.

4 g of amine, 10 g of aniline and 125 mg of beta zeolite in acid form treated with OMTS, as described in example 8, are fed into a glass autoclave. The autoclave is closed and is stirred at 150° C. for 6 hours.

The mass is then cooled at ambient temperature and the reaction solvent is removed by distillation at a reduced pressure.

The reaction product is analysed by H.P.L.C. according to the method of analysis described in the Journal für Praktische Chemie, Band 328,
Heft 1, 1986, 142–148.
Conversion: 100%;
selectivity at 4.4'-MDA: 57.73%;
selectivity at 2.4'+2.2'-MDA: 11.82%;
molar ratio 4.4'/(2.4'+2.2'): 4.88
trimers: 15.06%;
heavy particles: 14.29%.

EXAMPLE 19
Catalytic Test with Beta Zeolite Treated with Pure OMTS.

4 g of amine, 10 g of aniline and 125 mg of beta zeolite in acid form treated with pure OMTS, as described in example 9, are fed into a glass autoclave. The autoclave is closed and is stirred at 150° C. for 6 hours.

The mass is then cooled at ambient temperature and the reaction solvent is removed by distillation at a reduced pressure.

The reaction product is analysed by H.P.L.C. according to the method of analysis described in the Journal für Praktische Chemie, Band 328,
Heft 1, 1986, 142–148.
Conversion: 100%;
selectivity at 4.4'-MDA: 59.37%;
selectivity at 2.4'+2.2'-MDA: 16.72%;
molar ratio 4.4'/(2.4'+2.2'): 3.55
trimers: 14.07%;
heavy particles: 9.08%.

EXAMPLE 20 (COMPARATIVE)
Catalytic Test with Untreated Zeolite ZSM-12.

4 g of amine, 10 g of aniline and 500 mg of zeolite ZSM-12, prepared in accordance with U.S. Pat. No. 3,832,449 (1974) of the Mobil Oil Corporation, with a molar ratio of $SiO_2/Al_2O_3=102$, previously treated at 550° C. in an air flow in order to obtain zeolite in acid form, are fed into a glass autoclave. The autoclave is closed and is stirred at 150° C. for 6 hours.

The mass is then cooled at ambient temperature and the reaction solvent is removed by distillation at a reduced pressure.

The reaction product is analysed by H.P.L.C. according to the method of analysis described in the Journal für Praktische Chemie, Band 328, Heft 1, 1986, 142–148.
Conversion: 100%;
selectivity at 4.4'-MDA: 54.50%;
selectivity at 2.4'+2.2'-MDA: 30.36%;
molar ratio 4.4'/(2.4'+2.2'): 1.66
trimers: 10.76%;
heavy particles: 2.87%.

EXAMPLE 21
Catalytic Test with Zeolite ZSM-12 Treated with OMTS.

4 g of amine, 10 g of aniline and 500 mg of zeolite ZSM-12 in acid form treated with OMTS as described in example 10, are fed into a glass autoclave. The autoclave is closed and is stirred at 150° C. for 6 hours.

The mass is then cooled at ambient temperature and the reaction solvent is removed by distillation at a reduced pressure.

The reaction product is analysed by H.P.L.C. according to the method of analysis described in the Journal für Praktische Chemie, Band 328,
Heft 1, 1986, 142–148.
Conversion: 100%;
selectivity at 4.4'-MDA: 60.32%;
selectivity at 2.4'+2.2'-MDA: 19.39%;
molar ratio 4.4'/(2.4'+2.2'): 3.11
trimers: 12.93%;
heavy particles: 7.36%.

EXAMPLE 22 (COMPARATIVE)
Catalytic Test in a Fixed Bed Reactor with Untreated Beta Zeolite 5 cm3 of beta zeolite, CP 806BL PQ (previously calcined at 550° C. in a flow of air thus transforming it into acid form) with a molar ratio of $SiO_2/Al_2O_3=25$, compressed at 20 tonnes and sieved at 70–100 mesh are fed into a 390 mm long tubular reactor with a diameter of 12.5 mm. An amine mixture of 10% aniline in volume is then fed into the reactor at a temperature of 180° C., a pressure of 4 bars and an L.H.S.V. (Liquid Hourly Space Velocity) of 1 $h_{-1}$, relating to the active stage.

Samples are taken at the periods shown in table 1 which, after being removed from the solvent at reduced pressure, are analysed in accordance with the methodology described above. The conversion of the amine is complete in all the samples.

TABLE 1

| t.o.s. (h) | Ratio 4.4'/2.4' + 2.2' | 4.4' MDA % | 2.4' + 2.2' MDA % | Trimers % | Heavy Particles % |
|---|---|---|---|---|---|
| 4 | 1.15 | 57.88 | 37.91 | 12.69 | 3.43 |
| 5 | 1.11 | 53.85 | 38.42 | 11.84 | 3.65 |
| 21 | 1.19 | 59.16 | 37.32 | 12.03 | 2.83 |

After 21 hours of reaction, the speed of feed (LHSV=3.6 $h_{-1}$) is varied and the reaction mixture is fed in for a total t.o.s. (time on stream) of 44 hours without noting any phenomenon of deactivation. The conversion of amine always remains total. The results are recorded in table 2.

TABLE 2

| t.o.s. (h) | Ratio 4.4'/2.4' + 2.2' | 4.4' MDA % | 2.4' + 2.2' MDA % | Trimers % | Heavy Particles % |
|---|---|---|---|---|---|
| 24 | 1.71 | 58.41 | 30.08 | 11.76 | 2.24 |
| 26 | 1.75 | 51.24 | 30.46 | 9.27 | 2.23 |
| 28 | 1.75 | 50.87 | 30.44 | 8.96 | 2.27 |
| 44 | 1.81 | 50.98 | 29 | 10.84 | 2.85 |

After 44 hours of reaction, the speed of feed (LHSV=7.2 $h_{-1}$) is varied and the reaction mixture is fed in for a total t.o.s. (time on stream) of 51 hours without noting any phenomenon of deactivation. The conversion of amine always remains total. The results are recorded in table 3.

TABLE 3

| t.o.s. (h) | Ratio 4.4'/2.4' + 2.2' | 4.4' MDA % | 2.4' + 2.2' MDA % | Trimers % | Heavy Particles % |
|---|---|---|---|---|---|
| 47 | 1.82 | 48.15 | 29.04 | 10.16 | 3.15 |
| 49 | 1.85 | 51.45 | 28.88 | 10.01 | 2.87 |
| 50 | 1.85 | 48.23 | 29.31 | 8.75 | 2.61 |
| 51 | 1.84 | 52.32 | 27.36 | 12.5 | 2.98 |

After 51 hours of reaction, the concentration of feed (at the same LHSV=7.2 $h_{-1}$) is varied and the reaction mixture at 20% amine is fed in for a total t.o.s. of 71 hours without noting any phenomenon of deactivation. The conversion of amine always remains total. The results are recorded in table 4.

TABLE 4

| t.o.s. (h) | Ratio 4.4'/2.4' + 2.2' | 4.4' MDA % | 2.4' + 2.2' MDA % | Trimers % | Heavy Particles % |
|---|---|---|---|---|---|
| 52 | 1.92 | 59.22 | 27.82 | 10.87 | 2.08 |
| 56 | 1.98 | 59.84 | 27.18 | 10.55 | 2.78 |
| 71 | 1.98 | 58.07 | 26.22 | 11.92 | 3.79 |

After 71 hours of reaction, the concentration of feed (at the same LHSV=7.2 $h_{-1}$) is varied and the reaction mixture at 30% amine is fed in for a total t.o.s. of 71 hours without noting any phenomenon of deactivation. The conversion of amine always remains total. The results are recorded in table 5.

TABLE 5

| t.o.s. (h) | Ratio 4.4'/2.4' + 2.2' | 4.4' MDA % | 2.4' + 2.2' MDA % | Trimers % | Heavy Particles % |
|---|---|---|---|---|---|
| 74 | 1.98 | 60.03 | 27.04 | 11.19 | 1.73 |
| 76 | 2.05 | 60.23 | 26.13 | 11.23 | 2.41 |
| 78 | 2.07 | 59.31 | 25.36 | 12.7 | 2.63 |
| 92 | 2.09 | 60.3 | 25.47 | 12.01 | 2.22 |
| 96 | 2.15 | 60.47 | 24.6 | 12.59 | 2.34 |

EXAMPLE 23

Catalytic Test in a Fixed Bed Reactor with Beta Zeolite Treated with OMTS 5 cm3 of beta zeolite in acid form, treated with OMTS as described in example 5, compressed at 20 tonnes and sieved at 70–100 mesh are fed into a 390 mm long tubular reactor with a diameter of 12.5 mm. An amine mixture of 10% aniline in volume is then fed into the reactor at a temperature of 180° C., a pressure of 4 bars and an L.H.S.V. (Liquid Hourly Space Velocity) of 1 $h_{-1}$, relating to the active stage.

Samples are taken at the periods shown in table 6 which, after being removed from the solvent at reduced pressure, are analysed in accordance with the methodology described above. The conversion of the amine is complete in all the samples.

TABLE 6

| t.o.s. (h) | Ratio 4.4'/2.4' + 2.2' | 4.4' MDA % | 2.4' + 2.2' MDA % | Trimers % | Heavy Particles % |
|---|---|---|---|---|---|
| 4 | 1.82 | 53.05 | 31.51 | 8.53 | 6.63 |
| 5 | 1.75 | 45.9 | 29.3 | 11.84 | 12.2 |
| 21 | 1.81 | 55.9 | 32.01 | 6.93 | 5.05 |

After 21 hours of reaction, the speed of feed (LHSV=3.6 $h_{-1}$) is varied and the reaction mixture is fed in for a total t.o.s. of 44 hours without noting any phenomenon of deactivation. The conversion of amine always remains total. The results are recorded in table 7.

TABLE 7

| t.o.s. (h) | Ratio 4.4'/2.4' + 2.2' | 4.4' MDA % | 2.4' + 2.2' MDA % | Trimers % | Heavy Particles % |
|---|---|---|---|---|---|
| 24 | 2.8 | 69.24 | 24.7 | 2.56 | 3.45 |
| 26 | 2.6 | 63.62 | 24.49 | 7.97 | 3.74 |
| 28 | 2.75 | 67.57 | 24.58 | 4.9 | 2.86 |
| 44 | 2.85 | 68.47 | 24.02 | 3.83 | 3.53 |

After 44 hours of reaction, the speed of feed (LHSV=7.2 $h_{-1}$) is varied and the reaction mixture is fed in for a total t.o.s. of 51 hours without noting any phenomenon of deactivation. The conversion of amine always remains total. The results are recorded in table 8.

TABLE 8

| t.o.s. (h) | Ratio 4.4'/2.4' + 2.2' | 4.4' MDA % | 2.4' + 2.2' MDA % | Trimers % | Heavy Particles % |
|---|---|---|---|---|---|
| 47 | 3.3 | 70.35 | 21.33 | 5.26 | 3.01 |
| 49 | 3.16 | 71.99 | 21.55 | 3.44 | 2.94 |
| 50 | 3.22 | 70.66 | 22.32 | 4.87 | 2.02 |
| 51 | 3.22 | 66.29 | 20.15 | 3.59 | 9.89 |

After 51 hours of reaction, the concentration of feed (at the same LHSV=7.2 $h_{-1}$) is varied and the reaction mixture of 20% amine is fed in for a total t.o.s. of 71 hours without noting any phenomenon of deactivation. The conversion of amine always remains total.

The results are recorded in table 9.

TABLE 9

| t.o.s. (h) | Ratio 4.4'/2.4' + 2.2' | 4.4' MDA % | 2.4' + 2.2' MDA % | Trimers % | Heavy Particles % |
|---|---|---|---|---|---|
| 52 | 3.2 | 68.87 | 20.76 | 7.19 | 3.01 |
| 56 | 3.49 | 69.66 | 19.95 | 8.02 | 2.19 |
| 71 | 3.44 | 65.52 | 19.03 | 9.7 | 5.64 |

After 71 hours of reaction, the concentration of feed (at the same LHSV=7.2 $h_{-1}$) is varied and the reaction mixture at 30% amine is fed in for a total t.o.s. of 71 hours without noting any phenomenon of deactivation. The conversion of amine always remains total. The results are recorded in table 10.

TABLE 10

| t.o.s. (h) | Ratio 4.4'/2.4' + 2.2' | 4.4' MDA % | 2.4' + 2.2' MDA % | Trimers % | Heavy Particles % |
|---|---|---|---|---|---|
| 74 | 3.47 | 65.15 | 18.02 | 8.98 | 7.53 |
| 76 | 3.65 | 65.22 | 17.88 | 9.65 | 7.12 |
| 78 | 3.61 | 69.41 | 19.79 | 7.93 | 2.72 |
| 92 | 3.66 | 64.23 | 17.5 | 9.56 | 8.56 |
| 96 | 3.66 | 63.3 | 17.31 | 11.87 | 7.44 |

What is claimed is:

1. A process for the preparation of methane diphenyl diamine or a mixture of methane diphenyl diamine and its higher homologues having the general formula (I):

where R is independently selected from hydrogen, a C1 to C8 alkyl group, a C4 to C10 cycloalkyl group and a C6 to C12 aromatic group and n is a whole number from 1 to 5 so as to give a functionality from 2 and 6, which comprises carrying out the re-arrangement reaction of the intermediate having general formula (II):

in the presence of a zeolite in acid form with a "spaciousness index" from 2.5 to 19 modified on the surface by one or more organic silicon compounds having the general formula Si(OX)4 or SiX4, in which X represents independently a C1 to C20 alkyl group, a C4 to C20 cycloalkyl group, or a C6 to C20 aromatic or alkyl-aromatic group, optionally substituted with one or more halogen atoms which zeolite has been calcined.

2. A process according to claim 1, in which the zeolite comprises a synthetic crystalline material having the composition (III):

$$M^{n+}{}_{x/n}[(AlO_2)^-{}_x(SiO_2)]\cdot(H_2O)_p \quad [III]$$

where x is less than 1, p is a whole number greater than or equal to 1, M is a metal from Groups IA or IIA, or is a lanthanide, n is the valency of M, and where M may be partially or totally exchanged for $H^+$, $(NH_4)^+$, or for $(NR'_4)^+$ where R' is an alkyl group or an aryl group.

3. A process according to claim 2, in which the zeolite has a "spaciousness index" of 2.5 to 19.

4. A process according to claim 3, in which the zeolite is selected from beta zeolite, mordenite, ZSM-12, MCM-22 and ERB-1.

5. A process according to claim 1 in which the silanisation treatment of the acid zeolites is carried out by contacting the zeolite in a liquid comprising an organic silicon compound of formula Si(OX)4 and/or SiX4, as defined in claim 1 at a temperature of 20 to 80° C.

6. A process according to claim 5 in which the zeolite is contacted with an organic silicon compound two or more times with each contact stage being followed by removal of liquid and calcination.

7. A process according to claim 1 in which the zeolite is modified by the partial isomorphic substitution of aluminium by a metal selected from boron, iron and gallium, and then silanised.

8. A process according to claim 1 in which the zeolite is mixed with a binder.

9. A process according to claim 1 in which the zeolite is rearrangement reaction is carried out at a temperature of 50 to 250° C.

10. A process according to claim 1 in which the rearrangement reaction takes place in the presence of a solvent, selected from optionally substituted aliphatic hydrocarbons, optionally substituted aromatic hydrocarbons, halogenated aromatic hydrocarbons and aniline.

11. A process according to claim 10, in which the solvent is selected from aniline and a chlorinated aromatic solvent.

12. A process for the preparation of methane diphenyl diamine of general formula (I), where R is independently selected from hydrogen, a C1 to C8 alkyl group, a C4 to C10 cycloalkyl group and a C6 to C12 aromatic group and n is a whole number from 1 to 5 so as to give a functionality from 2 and 6, in which a rearrangement reaction is carried out by contacting a zeolite in acid form with a "spaciousness index" from 2.5 to 19 modified on the surface by on or more organic silicon compounds having the general formula Si(OX)4 or SiX4, in which X represents independently a C1 to C20 alkyl group, a C4 to C20 cycloalky group, or a C6 to C20 aromatic or alkyl-aromatic group, optionally substituted with one or more halogen atoms which zeolite has been calcined with a reaction mixture comprising aniline, or a derivative of aniline, and formaldehyde, or a compound capable of producing formaldehyde under the reaction conditions.

13. A process according to claim 12, in which the reaction is carried out with an excess of aniline, or its derivative, which acts as a reagent and a solvent.

14. A process for the production of a compound having general formula (I)

where R is independently selected from hydrogen, a C1 to C8 alkyl group, a C4 to C10 cycloalkyl group and a C6 to C12 aromatic group, and n is a whole number from 1 to 5 so as to give a functionality from 2 and 6, comprising:

(a) reacting aniline, or a derivative of aniline and formaldehyde, or a precursor of formaldehyde, so as to form an amine of formula (II) optionally in a solvent;

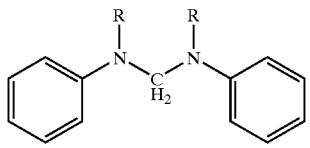 (II)

where R is as defined above, (b) removing water if present, from the amine (II) to a residual concentration of water of 3% or less by weight of the amine (II);

(c) optionally diluting the product of step (b) in a solvent;

(d) isomerising the amine (II) by feeding it into a reaction zone containing a zeolite in acid form with a "spaciousness index" of 2.5 to 19, modified on its surface, by one or more organic silicon compounds with the general formula Si(OX)4 and/or SiX4, in which X represents independently a C1 to C20 alkyl group, a C4 to C20 cycloalkyl group, or a C6 to C20 aromatic or alkyl-aromatic group, optionally substituted with one or more halogen atoms which zeolite has been calcined, and wherein the reaction zone in step d) is at an ambient pressure or such as to maintain the reagent mixture in a liquid state at a temperature of 50 to 250° C.;

(e) recovering the methane diphenyl diamine, and/or its higher homologues.

15. A process according to claim 14, in which the amine (II) is fed to the reaction zone of a vertical reactor through two or more lateral inlets.

16. A process according to any one of claims 14 or 15, in which the mixture obtained after isomerisation is totally or partially recycled in step a) or in step d).

17. A process for the production of a compound having general formula (I)

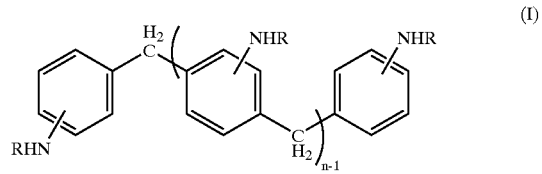 (I)

where R is independently selected from hydrogen, a C1 to C8 alkyl group, a C4 to C10 cycloalkyl group and a C6 to C12 aromatic group and n is a whole number from 1 to 5 so as to give a functionality from 2 and 6;

which comprises reacting aniline, or one of its derivatives, and formaldehyde, or one of its precursors, in a single reaction step presence of a zeolite in acid form with a "spaciousness index" of 2.5 to 19 modified on the surface by one or more organic silicon compounds having the general formula Si(OX)4 or SiX4, in which X represents independently a C1 to C20 alkyl group, a C4 to C20 cycloalkyl group, or a C6 to C20 aromatic or alkyl-aromatic group, optionally substituted with one or more halogen atoms which zeolite has been calcined.

* * * * *